United States Patent [19]

Nonn et al.

[11] Patent Number: 4,564,632
[45] Date of Patent: Jan. 14, 1986

[54] INSECTICIDAL AND ACARICIDAL AGENTS AND THEIR USE

[75] Inventors: Konrad Nonn; Karlheinz Wolf, both of Leverkusen; Johannes Haas, Grevenbroich; Volker Paulat, Monheim, all of Fed. Rep. of Germany

[73] Assignee: Bayer Aktiengesellschaft, Leverkusen, Fed. Rep. of Germany

[21] Appl. No.: 324,912

[22] Filed: Nov. 25, 1981

[30] Foreign Application Priority Data

Dec. 19, 1980 [DE] Fed. Rep. of Germany ....... 3048021

[51] Int. Cl.$^4$ .............................................. A01N 37/34
[52] U.S. Cl. ..................................... 514/522; 514/531
[58] Field of Search ....................... 424/304, 305, 358; 514/522, 531

[56] References Cited

U.S. PATENT DOCUMENTS

| | | | |
|---|---|---|---|
| 2,993,830 | 7/1961 | Hagge et al. | 424/358 |
| 3,948,636 | 4/1976 | Marks | 424/304 |
| 4,218,469 | 8/1980 | Fuchs et al. | 424/304 |
| 4,276,306 | 6/1981 | Fuchs et al. | 424/304 |

FOREIGN PATENT DOCUMENTS

| | | |
|---|---|---|
| 1121814 | 1/1962 | Fed. Rep. of Germany . |
| 2024625 | 1/1980 | United Kingdom . |

OTHER PUBLICATIONS

Bayer, II German Offenlegungsschrift 2840992, 9/21/78.
Bayer, III English Abstract of German Auslegeschrift 1,121,814, 1/11/62.
Hackh's Chemical Dictionary, 3rd edition, p. 787, McGraw-Hill Book Co., New York (1944).

*Primary Examiner*—Albert T. Meyers
*Assistant Examiner*—John W. Rollins
*Attorney, Agent, or Firm*—Sprung Horn Kramer & Woods

[57] ABSTRACT

The invention relates to insecticidal and acaricidal agents which contain water-insoluble active compounds and water-soluble oxyalkylation products of compounds prepared by adding styrenes onto phenols or naphthols, and which form a colloidal solution when diluted with water, and to their use.

5 Claims, No Drawings

INSECTICIDAL AND ACARICIDAL AGENTS AND THEIR USE

The invention relates to insecticidal and acaricidal agents which contain water-insoluble active compounds and water-soluble oxyalkylation products of compounds prepared by adding styrenes onto phenols or naphthols, and which form colloidal solutions when diluted with water, and to their use.

The styrene is preferably optionally alkylated styrene and in particular a compound of the formula

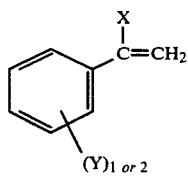

in which

X represents hydrogen or methyl and

Y represents hydrogen or $C_1$-$C_4$-alkyl.

Examples which may be mentioned are styrene, vinyltoluene and α-methylstyrene.

Preferred phenols have the formula

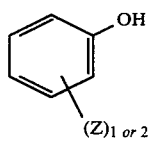

wherein

Z represents hydrogen, $C_1$-$C_4$-alkyl or phenyl.

Of these phenols, phenol and the isomeric cresols, xylenols and hydroxydiphenyls are particularly suitable.

Preferred naphthols are, in addition to α- and β-naphthol, homologues of these naphthols with 1 or 2 methyl groups.

The addition products are prepared in a known manner, advantageously in the presence of catalysts, such as sulphuric acid, p-toluenesulphonic acid or zinc chloride. The addition products can be subjected to oxyalkylation in the form of single substances, but it is also possible to use mixtures such as are in general initially obtained in the preparation of these products.

The oxyalkylation products are known. They can be prepared in a manner which is known per se, for example by the method in German Auslegeschrift No. 1,121,814.

Preferred oxyalkylation products are those which are obtained by reacting addition products of 1 to 3 mols of styrene or vinyltoluene and 1 mol of phenol with 8–50 mols of ethylene oxide or propylene oxide.

Compounds of the formula

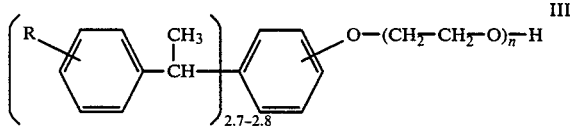

wherein

R denotes hydrogen or methyl and n denotes a number from 12–30, are especially preferred.

Water-insoluble or virtually water-insoluble insecticides and acaricides which may be mentioned are, in particular, cyclopropanecarboxylic acid esters and isopropylphenylacetic acid esters. The benzyl and phenoxybenzyl esters, which are described, for example in German Offenlegungsschriften Nos. 2,709,264, 2,730,515, 2,840,992 and 2,923,217, may be especially mentioned.

The agents according to the invention can contain other additives, such as agents for reducing their viscosity, for example formamide, glycol, glycol ethers and water and/or agents for characterising them, for example colorants, and/or agents for reducing foam formation when they are used as sprays, for example, tri-n-butyl phosphate.

Preferred agents contain 0.1–40%, preferably 1–20%, of insecticide or acaricide, 0.2–90%, preferably 2–40%, of oxyalkylation products according to the invention, 0–90%, preferably 20–70%, of agents for reducing the viscosity, 0–2% of characterising agents and/or 0–5% of anti-foaming agents.

Because the insecticides and acaricides have a very high activity, they are used in very dilute form. Active compound concentrations in water of less than 100 ppm are frequently sufficient to achieve a 100% destruction of numerous insects. In order to facilitate exact metering for the user, it is frequently appropriate to formulate the agent according to the invention with an active compound content of only 0.5–5%, and not to choose the maximum possible concentration of active compound.

Insecticidal and acaricidal agents which contain the above water-insoluble or virtually water-insoluble active compounds, non-ionic emulsifiers and other additives are known. In German Offenlegungsschriften Nos. 2,709,264, 2,840,992 and 2,923,217, non-ionic emulsifiers which are mentioned are: fatty acid polyglycol esters, fatty alcohol polyglycol ethers, alkylaryl polyglycol ethers and alkylphenol polyglycol ethers. If these known concentrates are diluted with water, for example to form a spray liquor or for mothproofing textiles containing wool, turbid emulsions are obtained. When these emulsions are left to stand, they demix, so that stirring or shaking is necessary to achieve uniform distribution of the active compound in the water.

It has now been found that, if a minimum amount of the oxyalkylated addition product is present, relative to the active compound content, the agents according to the invention give a colloidal solution when diluted with water in any desired ratio. A colloidal solution is defined, for example, by A. F. Holleman and E. Wiberg in "Lehrbuch der anorganischen Chemie" ("Textbook of Inorganic Chemistry"), 71st–80th Edition (1971), pages 505 and 506. The minimum amount of oxyalkylated addition product can easily be determined by simple preliminary experiments. At least 1 part by weight of oxyalkylation product is usually required per part by weight of active compound. In principle, there is no upper limit for the weight ratio of active compound:surface-active agent. From an industrial viewpoint, the ratio 1:20 should not be exceeded. If the particularly preferred compound of the formula (III) is used, about 1.5 to 3.5 parts by weight of this surface-active agent per part by weight of active compound from the phenoxybenzylcyclopropanecarboxylate and isopropylphenylacetate series are particularly advantageous from an industrial viewpoint.

No droplets of the water-insoluble active compound can be observed under an optical microscope. Even if polarised light is used, the dilution of the concentrate according to the invention with water appears as a clear solution under the optical microscope. If these solutions are irradiated with a laser, a scattering effect as for micellar solutions can be observed (compare H. Sonntag, Lehrbuch der Kolloidwissenschaft (Textbook of Colloid Science), VEB Deutscher Verlag der Wissenschaften, Berlin 1977; page 257 et seq.). In these solutions, the surface-active agents are in the form of micelles in which the active compounds are solubilised. The size of the micelles can be determined by laser light-scattering measurements and evaluation thereof with the aid of autocorrelation spectroscopy.

If the solubilising capacity of the micelles is exceeded by adding dissolved active compound, turbidity and the appearance of drops of emulsion are observed.

EXAMPLE 1

660 parts by weight of ethylene oxide are passed, at 130° C. in the presence of 4 parts by weight of potassium hydroxide, into 419 parts by weight of an α-tolylethylphenol mixture which has been obtained by reacting 325 parts by weight of p-methylstyrene with 94 parts by weight of phenol in the presence of sulphuric acid as a catalyst. The resulting highly viscous oil is a mixture of numerous substances, the average composition of which corresponds to the formula (III) in which R represents methyl and n represents the number 15.

EXAMPLE 2

A substance mixture, the average composition of which corresponds to the formula (III) in which R represents methyl and n represents the number 30, is obtained analogously to Example 1 by the introduction of 1,320 parts by weight of ethylene oxide.

EXAMPLE 3

100 parts by weight of 4-fluoro-3-phenoxy-benzyl 3-(2,2-dichlorovinyl)-2,2-dimethyl-cyclopropanecarboxylate and 250 parts by weight of the oxyalkylation product described in Example 1 are dissolved in 650 parts by weight of diethylene glycol monoethyl ether.

If 1 part by weight of this solution is distributed in 50 parts by weight of water, a clear solution is obtained. Laser light-scattering measurement ($\lambda = 568$ nm at a scattering angle of 90°) and evaluation thereof with the aid of autocorrelation spectroscopy gives a mean diameter for the micelles of 13 nm.

EXAMPLE 4

100 parts by weight of 2,3,4,5,6-pentafluorobenzyl 3-(2,2-dichlorovinyl)-2,2-dimethyl-cyclopropanecarboxylate and 500 parts by weight of the oxyalkylation product described in Example 2 are dissolved in 400 parts by weight of dimethylformamide.

If 1 part by weight of this solution is stirred into 50 parts by weight of water, a clear solution is obtained. Laser light-scattering measurement according to Example 3 shows micelles with a mean diameter of 22 nm.

EXAMPLE 5

100 parts by weight of α'-cyano-4'-fluoro-3'-phenoxybenzyl 2-isopropyl-4-trifluoromethoxyphenylacetate and 200 parts by weight of the oxyalkylation product described in Example 1 are dissolved in 500 parts by weight of ethylene glycol and 200 parts by weight of water.

If 1 part by weight of this solution is stirred into 50 parts by weight of water, a clear solution is obtained. Laser light-scattering measurement shows a mean diameter for the micelles of 13 nm.

EXAMPLE 6

300 parts by weight of α-cyano-3-phenoxy-4-fluorobenzyl 2,2-dimethyl-3-(2,2-dichlorovinyl)-cyclopropanecarboxylate and 600 parts by weight of the oxyalkylation product described in Example 1 are mixed, with the addition of 100 parts by weight of diethylene glycol monoethyl ether. If 1 part by weight of this viscous mixture is stirred into 100 parts by weight of water, a clear solution is obtained. On the basis of laser light-scattering measurement, this solution contains micelles with a mean diameter of 13 nm.

EXAMPLE 7

10 parts by weight of the carboxylic acid benzyl ester from Example 6 are mixed with 30 parts by weight of the oxyalkylation product described in Example 1, and a total of 960 parts by weight of water are added in portions, whilst stirring. After the mixture has been stirred for three hours, a clear solution is obtained which remains clear when diluted with any desired amounts of water.

EXAMPLE 8

Woollen yarn is introduced, at 40° C. and in a liquor ratio of 1:10, into a dyebath containing, per liter of water, 2 g of Acid Red 249 (C.I.No. 18 134), 10 g of sodium sulphate, 3 g of acetic acid and 1 g of the solution described in Example 7. The bath is then heated to 100° C. and the dyeing is finished in a customary manner. The resulting red-coloured wool possesses good protection from being eaten by moths and beetles. This protection still remains even after the wool has been washed repeatedly.

EXAMPLE 9

A mixed yarn consisting of 80% of wool and 20% of polyamide is introduced, at 40° C. and in a liquor ratio of 1:10, into a dyebath containing, per liter of water, 2 g of Acid Orange 33 (C.I.No. 24 780), 3 g of ammonium sulphate, 1 g of acetic acid, 1.5 g of a condensation product of phenolsulphonic acid, di-(hydroxyphenyl)-sulfone and formaldehyde, 2 g of a condensation product of naphthalenesulphonic acid and formaldehyde and 1 g of the solution described in Example 7. The bath is then heated to 100° C. and the dyeing is finished in a customary manner. The orange-coloured wool content of the mixed yarn thus treated has a good protection against being eaten by moths and beetles. This protection remains even after repeated washing.

EXAMPLE 10

A mixed yarn consisting of 45% of wool and 55% of polyester is introduced, at 40° C. and in a liquor ratio of 1:10, into a dyebath containing, per liter of water, 3 g of Disperse Blue 56 (C.I.No. 63 285), 1.5 g of a blue dyestuff of the formula

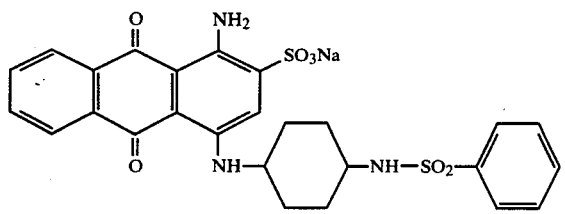

1 g of acetic acid, 2 g of a condensation product of naphthalenesulphonic acid and formaldehyde, 3 g of a mixture of methyl cresotinate and an addition product of 30 mols of ethylene oxide and castor oil and 0.45 g of the solution described in Example 7. The bath is then heated to 100° C. and the dyeing is finished in a customary manner. The blue-coloured wool content of the solid-dyed mixed yarn thus treated has a good protection against being eaten by moths and beetles. This protection remains even after repeated washing.

EXAMPLE 11

Raw wool is washed and mothproofed in a Leviathan by the continuous washing process. For this, the liquor in the last tank of the Leviathan is adjusted to a pH value below 7 with acetic acid, and 1 g of the solution described in Example 7 is added per liter of water. The treatment is carried out at 40°–60° C.

To maintain the concentration in the treatment bath, the bath is topped up with 10 g of the solution described in Example 7 per kg of raw wool. The bath is continuously topped up with the aqueous solution throughout the entire treatment period. The raw wool thus treated has a good protection against being eaten by moths and beetles. It can be subjected to all the further processing operations customary in the textile industry without its technological properties being impaired.

We claim:

1. An insecticidal and acaricidal composition, which when diluted with water forms a clear colloidal solution, comprising
    (a) an insecticidally and acaricidally active water-insoluble benzyl or phenoxybenzyl ester of a cyclopropanecarboxylic acid or an isopropylphenylacetic acid, and
    (b) a water soluble product produced by condensing 1 mol of phenol with 1 to 3 mols of styrene or vinyltoluene and reacting the condensation product with 8 to 50 mols of ethylene oxide or propylene oxide, the weight ratio of (a) to (b) ranging from 1:1–20.

2. A composition according to claim 1, comprising by weight
    0.1 to 40% of (a),
    0.2 to 90% of (b),
    up to 90% of a viscosity-reducing agent,
    up to 2% of a characterising agent, and
    up to 5% of an anti-foaming agent.

3. A clear colloidal solution in water of a composition according to claim 2.

4. A clear colloidal solution in water of a composition according to claim 1.

5. A composition according to claim 1, wherein the ester is
4-fluoro-3-phenoxy-benzyl 3-(2,2-dichlorovinyl)-2,2-dimethyl-cyclopropanecarboxylate,
2,3,4,5,6-pentafluorobenzyl 3-(2,2-dichlorovinyl)-2,2-dimethyl-cyclopropanecarboxylate or
α-cyano-3-phenoxy-4-fluoro-benzyl 2,2-dimethyl-3-(2,2-dichlorovinyl)-cyclopropanecarboxylate.

* * * * *